United States Patent [19]

Malabarba et al.

[11] Patent Number: 4,645,827
[45] Date of Patent: Feb. 24, 1987

[54] GLYCOPEPTIDE ANTIBIOTIC L 17054

[75] Inventors: Adriano Malabarba, Milano; Paolo Strazzolini, Fiume Veneto; Angelo Borghi, Milano; Bruno Cavalleri, Milano; Carolina Coronelli, Milano, all of Italy

[73] Assignee: Gruppo Lepetit S.p.A., Milano, Italy

[21] Appl. No.: 591,096

[22] Filed: Mar. 19, 1984

[30] Foreign Application Priority Data

Mar. 22, 1983 [GB] United Kingdom ................ 8307847

[51] Int. Cl.$^4$ ..................... C07C 103/52; C07H 17/08
[52] U.S. Cl. .................................. 530/322; 536/16.8; 536/18.1
[58] Field of Search ...................... 536/16.8, 18.1, 7.1; 424/180, 181; 200/112.5 R; 530/322

[56] References Cited

U.S. PATENT DOCUMENTS

| 4,239,751 | 12/1980 | Coronelli et al. | 424/120 |
| 4,269,971 | 5/1981 | Yamagishi et al. | 424/181 |
| 4,357,325 | 11/1982 | Ose et al. | 536/7.1 |
| 4,479,897 | 10/1984 | Hunt et al. | 536/16.8 |
| 4,485,102 | 11/1984 | Waite | 424/123 |

Primary Examiner—Johnnie R. Brown
Assistant Examiner—Elli Peselev
Attorney, Agent, or Firm—Stephen L. Nesbitt

[57] ABSTRACT

The present invention is directed to the essentially pure preparation of an antibiotic substance arbitrarily designated antibiotic L 17054. This antibiotic substance is obtained from the known antibiotic substance named teicoplanin (formerly teichomycin) by chemical treatment. The new compound and the pharmaceutically acceptable salts possess antimicrobial activity.

2 Claims, 3 Drawing Figures

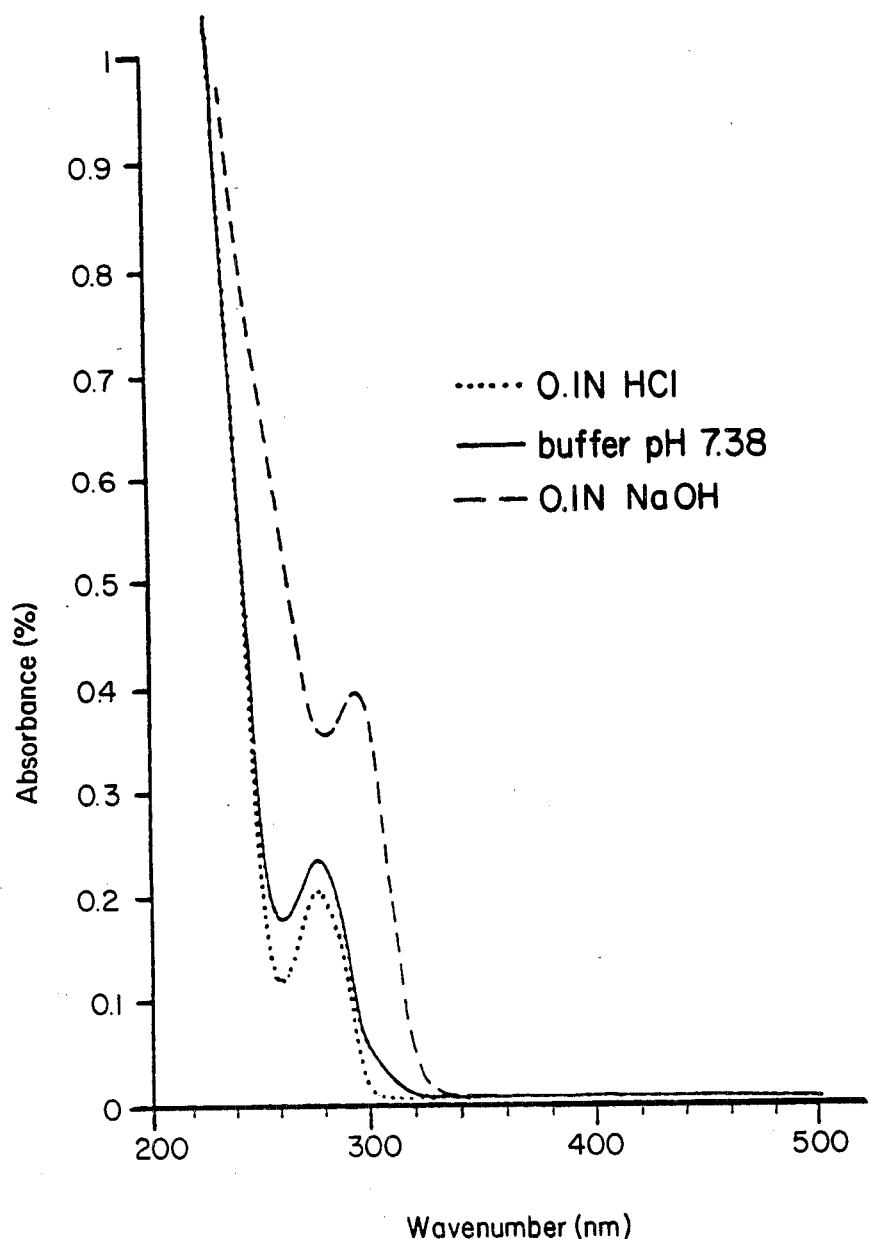
FIG. 1  UV spectrum of antibiotic L 17054

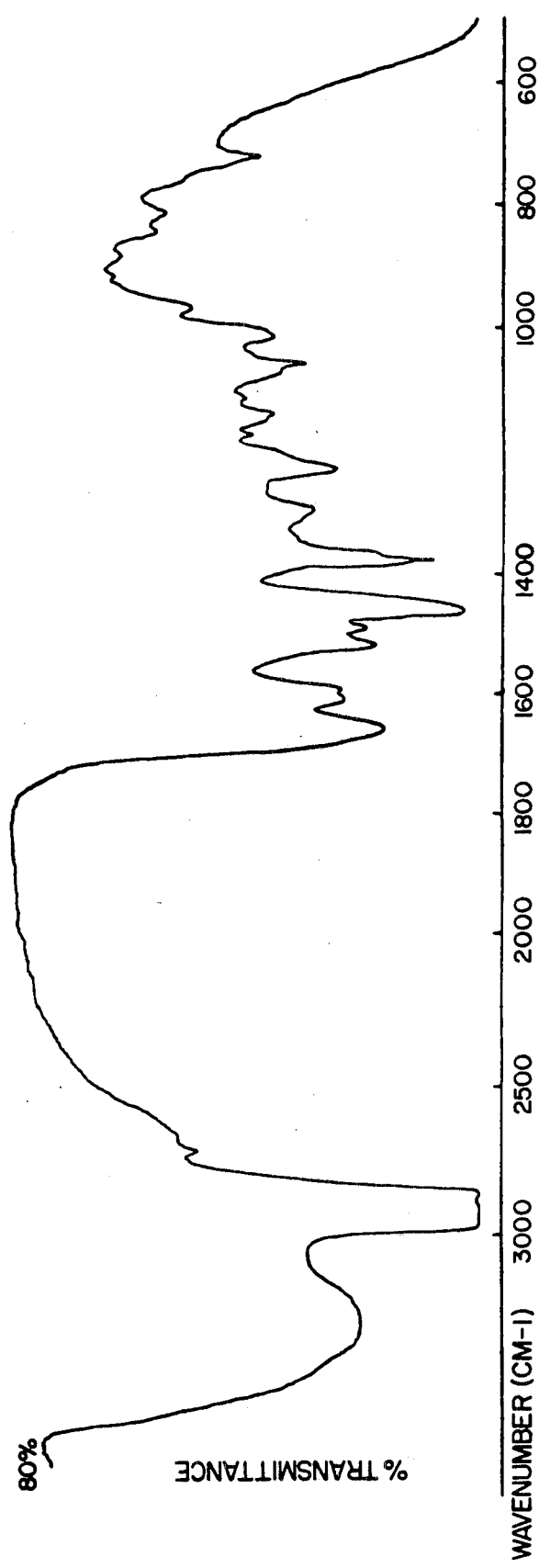
Fig. 2 IR spectrum of antibiotic L17054

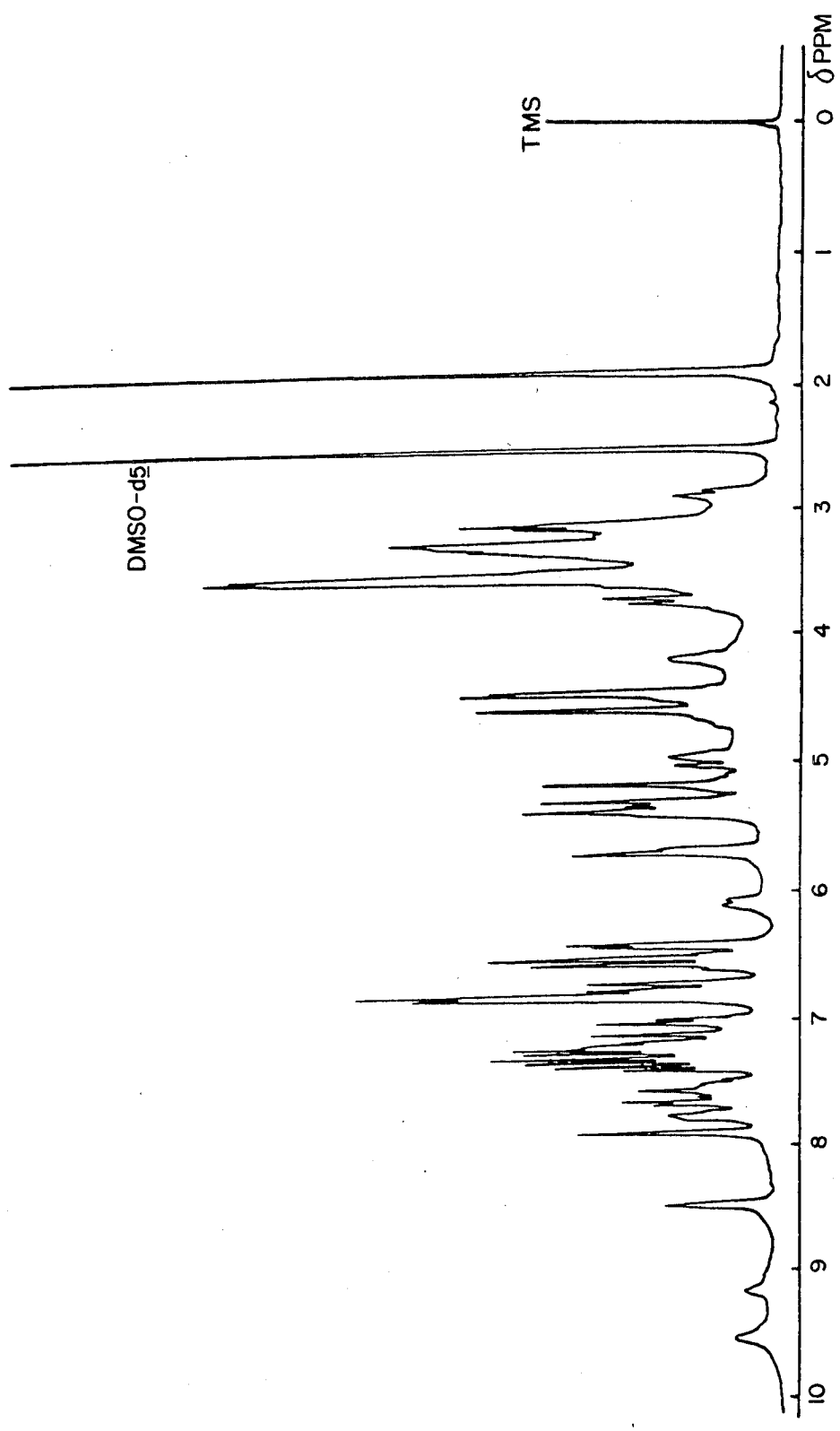
Fig. 3 ¹H NMR spectrum of antibiotic L17054

GLYCOPEPTIDE ANTIBIOTIC L 17054

The present invention is directed to the essentially pure preparation of an antibiotic substance arbitrarily designated antibiotic L 17054. This antibiotic substance is obtained from Teicoplanin $A_2$ by chemical treatment. Teicoplanin is the international non-proprietary name (INN) of the antibiotic substance formerly named teichomycin which is obtained by cultivating the strain *Actinoplanes teichomyceticus* nov.sp. ATCC 31121 in a culture medium containing assimilable sources of carbon, nitrogen and inorganic salts (see U.S. Pat. No. 4,239,751). According to the procedure described in the above cited patent an antibiotic mixture containing Teicoplanin $A_1$, $A_2$ and $A_3$ is recovered from the separated fermentation broth by extraction with a suitable water insoluble organic solvent and precipitation from the extracting solvent according to common procedures. Teicoplanin $A_2$, which is the major factor of the isolated antibiotic complex, is then separated from the antibiotic mixture thus obtained by means of column chromatography on Sephadex ®.

British Patent Application Publication No. 2121401 discloses that antibiotic teicoplanin $A_2$ actually is a mixture of five closely related co-produced factors.

Surprisingly, it has now been found that it is possible to transform teicoplanin $A_2$, its single factors or mixtures thereof, into a different antimicrobial derivative which is denominated antibiotic L 17054. This transformation is essentially a chemical transformation. More particularly, the mild and controlled acid hydrolysis of an antibiotic substance selected from teicoplanin, an individual constituent factor or a mixture thereof, gives antibiotic L 17054. The concentration of the acid in the hydrolysis medium was found to be a critical parameter. In general, hydrochloric acid concentrations lower than 1N can be usefully used. More particularly, the concentration of the hydrochloric acid is preferably between 0.1N and 0.8N, while the preferred hydrochloric acid concentration is about 0.5N.

As it is apparent to the man skilled in the art, similar results can be obtained by using substantially equivalent acidic conditions, such as another mineral or organic acid of similar strength at similar concentration. The temperature can be varied depending on the strength of the mineral acid used and the reaction time. Good result are obtained by carrying out the reaction at a temperature between 70°–90° C., especially when using hydrochloric acid about 0.5N.

The reaction time, in turn, varies very much depending on the specific reaction conditions, i.e. type and concentration of the acid and reaction temperature. In general, the reaction is complete in about 45–90 minutes or more.

Although, in general, the process of the invention is preferably conducted by using a single mineral acid, it may be possible to use a mixture of different acids in order to obtain reaction conditions similar to those outlined above when dealing with a single hydrolyzing agent. In general, the possibility of these substitutions and the suitable mixtures of hydrolytic agents are apparent to the skilled man who is also able to select the proper reaction temperature and time on the basis of what is disclosed in the present application and what is generally known in the art. Each reaction step is monitored, as known in the art, by means of TLC or preferably HPLC technics. Also chromatographic techniques coupled with bioassay tests (e.g. autobioassay) using microorganisms susceptible to the antibiotic substance L 17054 can be conveniently used.

The compound which forms, antibiotic L 17054, is in general insoluble in highly concentrated mineral acids and precipitates. Precipitation may be aided as known in the art, for instance, by addition of non-solvents. The recovered crude product is then purified preferably by means of chromatographic techniques. In particular, partition column chromatography is preferred. A preferred absorbent is in this case uniform particle-size silica gel.

The eluent is preferably a mixture of acetonitrile and water, but eluting mixtures of solvents having a similar polarity can be conveniently used. The preferred eluent mixture is represented by a linear gradient mixture of acetonitrile and water from about 85:15 to about 70:30. The flow rate is preferably about 357 ml/h. Before passing this eluting mixture through the column, the column is developed using mixtures acetonitrile:water of increasing water content (from 1% up to 15%).

The elution is monitored by chromatographic assays, preferably HPLC.

The collected fractions are pooled according to the antibiotic content. Pure antibiotic L 17054 is then recovered by following known per se techniques, such as precipitation by non-solvents, filtration or extraction with solvents, concentration to a small volume and precipitation.

Another purification technique which can be conveniently used is represented by a reverse-phase partition chromatography. A preferred adsorbent is, in this case, silanized silica gel of uniform particle size, 0.06–0.2 mm silanized silica gel being the preferred adsorbent. The eluent is preferably a mixture of aqueous ammonium formate and acetonitrile. The aqueous ammonium formate is preferably 0.2% aqueous ammonium formate, but eluting mixtures having a similar polarity may conveniently be used. The preferred eluent is a linear gradient mixture of 0.2% aqueous ammonium formate and acetonitrile at a ratio from 95:5 to about 80:20. The elution is monitored by usual assays, and preferably by HPLC analysis.

Antibiotic L 17054 containing fractions are pooled, the volatiles are distilled off under vacuum and the residual aqueous solution is preferably applied to a silanized silica gel column prepared in water. The column is then preferably developed with a 1:1 mixture of acetonitrile and water, after having washed thoroughly with water. The pure preparation of antibiotic L 17054 is finally recovered by using known per se techniques as above described.

A preferred procedure for recovering the pure antibiotic L 17054 from an aqueous solution is to adjust the pH of the solution about 3.5 and add a non-solvent, such as acetone, to precipitate the desired product.

Physico-Chemical Characteristics of Antibiotic L 17054

Antibiotic L 17054 has the following characterics:

(a) the specific rotation $[\alpha]_D^{20}$ is $-34°$ (c=1%, DMF).

(b) it is freely soluble in water at pH>8.0, in dimethylformamide, dimethylsulfoxide, propyleneglycol and methylcellosolve; slightly soluble in methanol; almost insoluble in ethyl ether and acetone.

(c) an ultraviolet absorption spectrum, which is reported in FIG. 1 of the accompanying drawings, which has the following absorption maxima:

in 0.1N hydrochloric acid:
λ$_{max}$ 278 nm (E$_{1\ cm}$$^{1\%}$=60.6)
in 0.1N sodium hydroxide:
λ$_{max}$ 297 nm (E$_{1\ cm}$$^{1\%}$=118.8)
in phosphate buffer pH 7.4:
λ$_{max}$ 277 nm (E$_{1\ cm}$$^{1\%}$=70.3)

(d) an infrared absorption spectrum in nujol, shown in FIG. 2 of the accompanying drawings, with the following absorption maxima (cm$^{-1}$): 3700–2000, 2970–2850 (nujol), 1655, 1610, 1595, 1515, 1490, 1460 (nujol), 1375 (nujol), 1300, 1230, 1145, 1060, 1020, 970, 890, 850, 820;

(e) an elemental analysis, after the sample has been previously dried at about 140° C. under inert atmosphere (weight loss=7.8%), which indicates the following approximate percentage composition (average): carbon 55.46%; hydrogen, 4.50%; nitrogen 7.20%; chlorine 4.67%; ashes 0.2%

(f) it has the following R$_f$ values in the TLC systems indicated below:

| Elution system (v/v) | R$_f$ value |
| --- | --- |
| (I) Acetonitrile:water 75:25 (silica gel Merck 60 F$_{254}$) | 0.32 |
| (II) Acetonitrile:5% aqueous sodium sulfate 30:70 (silica gel Merck silanized 60 F$_{254}$) | 0.61 |

Visualization: UV-light at 254 nm; 3% ethanolic ninhydrine; 1% methanolic fluorescamine;

(g) a retention time (t$_R$) of 8.3 minutes when analyzed by HPLC using a 150×4.0 mm column Zorbax ® ODS (5–6 μm) (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$:acetonitrile (9:1) buffered at pH 6.0 with 0.1N NaOH; solution B: 25 mM NaH$_2$PO$_4$:acetonitrile (3:7) buffered at pH 6.0 with 0.1N NaOH), with a flow rate of 2 ml/min.; (internal standard: 3,5-dihydroxytoluene t$_R$ 5.60 minutes)

(h) the $^1$H NMR spectrum registered at 270 MHz in DMSO-d$_6$ at 60° C. and with a sample concentration of 20 mg/ml is reported in FIG. 3 (internal standard, TMS δ=0.00 ppm).

Some of the $^1$H NMR data obtained after D$_2$O exchange and selective decoupling experiments are as follows (δ ppm, multiplicity): 1.88, s; 2.85, d; ~3.5, dd; 3–4; 4.20, d; 4.48, d; 4.50, d; 4.62, s; 4.96, ddd; 5.18, d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d;

(i) a potentiometric titration profile which shows three titration slopes with pH½ values equal to 5.0 (one equivalent), 7.0 (one equivalent), and 11 (five equivalents) in methylcellosolve:water 4:1 upon titration with 0.01N NaOH of the solution of the test compound containing an excess of 0.01N HCl in the same solvent mixture (l) an acidic function capable of forming salts
(m) a basic function capable of forming salts
(n) two sugar residues which are D-mannose and N-acetyl-D-glucosamine.

On the basis of the physico-chemical data and by comparison with the structures known for other glycopeptidic antibiotic substances, such as vancomycin and ristocetin, the following structure can tentatively be attributed to antibiotic L 17054:

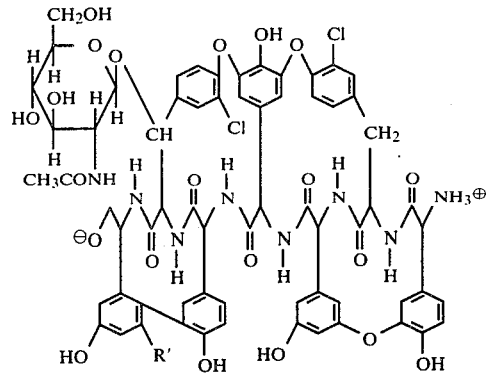

wherein R' represents the group of formula

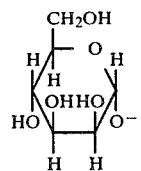

U.S. Pat. No. 4,239,751 discloses a minor component of antibiotic 8327 factor A and names it "teichomycin factor A$_3$". Only a method for obtaining it by chromatographic separation of antibiotic 8327 factor A as well as its paper chromatography behaviour and in vitro activities are therein reported.

It was found that antibiotic L 17054 has chromatographic features very similar to teichomycin factor A$_3$. However, a qualitative difference between the two compounds is represented by the fact that their antimicrobial activity are greatly different. In particular, antibiotic L 17054 possesses an in vitro anti-gram positive activity which is about five times higher than teicomycin A$_3$ for most of the strains.

In addition, the physico-chemical data demonstrates that antibiotic L 17054 is a pure and unitary compound.

Antibiotic L 17054 possesses acid and basic functions capable of forming salts respectively with bases and acids and therefore it can be transformed into its pharmaceutically acceptable acid and/or basic addition salts according to procedures known per se in the art. The acid addition salts are prepared as known in the art, preferably by using mineral acids or rather strong acids in general such as hydrohalic, sulfuric, phosphoric, nitric, acetic, citric, aspartic, methanesulfonic, toluenesulfonic, or sulfanilic acid.

The basic addition salts, such as the alkali metal, the alkaline earth metal, the ammonium and organic ammonium salts such as the alkylammonium salts are prepared as known in the art. In some instances they can be preferred in view of their easy preparation and desirable solubility properties. The basic addition salts also encompass basic aminoacid addition salts such as the lysine, arginine or glycine salts.

In view of the similarity of the properties of antibiotic L 17054 and its salts, what is said in the present application when dealing with the biological activities of antibiotic L 17054 applies also to its pharmaceutically acceptable salts.

The in vitro antibacterial activity of antibiotic L 17054, which showed to be mainly active against grampositive bacteria, was determined by using the two-fold dilution method in microtiter system. Isosensitest broth (Oxoid) and Todd-Hewitt broth (Difco) were used for Staphylococci and Streptococci respectively. Broth cultures were diluted so that the final inoculum was about $10^4$ colony forming units/ml (CFU/ml). Minimal inhibitory concentration (MIC) was considered as the lowest concentration which showed no visible growth after 18-24 h incubation at 37° C. The obtained results are summarized in TABLE I below:

TABLE I

| In vitro antibacterial activity of antibiotic L 17054 | |
| --- | --- |
| Microorganism | MIC (µg/ml) |
| Staphylococcus aureus ATCC 6538 | 0.4 |
| Staplylococcus aureus Tour | 0.4 |
| Staplylococcus aureus Tour (Isosensitest broth + 30% bovine serum) | 0.8 |
| Staphylococcus epidermidis ATCC 12228 | 0.4 |
| Streptococcus pyogenes C 203 | 1.6 |
| Streptococcus dysgalactiae ATCC 9926 | 1.6 |
| Streptococcus faecalis ATCC 7080 | 1.6 |
| Streptococcus pneumoniae UC 41 | 1.6 |

The antimicrobial activity of the compound of the invention is confirmed also in in vivo experiments.

An experimental infection was induced in mice by intraperitoneally administering a suspension of *S. pyogenes* C 203. Inocula had been adjusted so that the untreated animals die of septicemia within 48 h. Animals were treated subcutaneously with the compound of the invention once a day for three days starting immediately after infection.

The $ED_{50}$ value was calculated on the $10^{th}$ day by the method of Spearman and Karber (D. J. Finney "Statistical Methods in biological assay", Griffin, page 524, 1952) on the basis of the percentage of survival at each dose. In the above conditions the $ED_{50}$ value of antibiotic L 17054 is 2.64 mg/kg/day.

The approximate acute toxicity in mice (i.p.) of antibiotic L 17054 was evaluated according to methods known in the art and the approximate $LD_{50}$ was found to be about 1660 mg/kg in mice administered by i.m. route.

In view of the above, the compound of the present invention can effectively be employed as the active ingredient of antimicrobial preparations used in human and veterinary medicine for the prevention and treatment of infectious diseases caused by pathogenic bacteria which are susceptible to said active ingredients. The compounds of the present invention can be administered orally, topically or parenterally. However, the parenteral and topical routes of administration are preferred. Particularly preferred are those pharmaceutical formulations suitable for intramuscular administration. Depending on the route of admnistration, these compounds can be formulated into various dosage forms. The formulation of suitable pharmaceutical compositions can be carried out by the skilled man according to the general common knowledge in the art with the auxilium of reference books, such as the "Remington's Pharmaceutical Sciences" Handbook, Mack Publishing Company, U.S.A., 15th Edition, 1975.

For topical use the compounds of the present invention may be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-liquid form. Topical applications may be formulated in hydrophobic or hydrophilic bases as ointments, creams, lotions, paints, or powders. Compositions for injection may take such forms as suspensions, solutions, or emulsions in oily or aqueous vehicles, and may contain formulatory agents such as preservative, suspending, stabilizing and/or dispersing agents.

Alternatively, the active ingredient may be in powder form for reconstitution, at the time of delivery, with a suitable vehicle, such as sterile water.

The active compound may also be formulated into suppositories for rectal, vaginal or urethral administration. The excipient are those usually used in these preparations such as polyvinylpyrrolidone, cocoa butter, triglycerides of $C_{12}$-$C_{18}$ fatty acids, polyethylene glycols and surface-active agents.

The amount of compound administered will vary with the severity of the infection, the nature and body weight of the patient, the type and formulation in which the active ingredient is to be administered, the mode of administration, the general health status of the patient, and the interval between each subsequent administration.

In consideration of the above parameters, sometimes it may be necessary to deviate from the dosage-range indicated. In general, antibiotic L 17054 and its pharmaceutically acceptable salts are effective at a daily dosage comprised between about 0.1 and about 20 mg of active ingredient per Kg of body weight, preferably divided in 2 to 4 administrations per day.

Particularly desirable compositions are those prepared in the form of dosage units containing from about 5 to about 250 mg of the active principle per unit.

Representative examples of preparation of pharmaceutical compositions are as follows:

A parenteral solution is prepared with 100 mg of antibiotic L 17054 sodium salt dissolved in 2 ml of sterile water for injection A parenteral solution is prepared with 250 mg of L 17054 sodium salt dissolved in 3 ml of sterile water for injection A topical ointment is prepared with 200 mg of L 17054, 600 mg of polyethylene glycol 4000 U.S.P., 1.2 g of polyethylene glycol 400 U.S.P.

Besides their activity as medicaments, the compounds of the present invention can be used as animal growth promoters.

For this purpose the compounds of the invention are administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference.

EXAMPLE 1

Preparation of antibiotic L 17054

5 g of teicoplanin are added to 60 ml of 0.5N aqueous hydrochloric acid pre-heated to 80° C. with vigorous stirring.

Stirring is continued and the temperature is maintained at about 80° C. for 30 minutes. Then, the mixture is rapidly filtered, the filtrate is cooled to 0°–5° C. and 6N hydrochloric acid (10 ml) is added. The resulting suspension is stirred for about 15 minutes while keeping the temperature at 0°–5° C. The precipitate is collected, washed with 20 ml of cold 1N HCl and then with ethyl ether, and dried under reduced pressure at room temperature resulting in crude antibiotic L 17054 (4.5 g).

EXAMPLE 2

Purification of crude antibiotic L 17054

7.5 g of crude antibiotic L 17054 obtained as in the foregoing example are dissolved in 90% methanol (500 ml), silica gel (Merck 0.06–0.2) is added and the solvent is completely evaporated off.

The residue is then applied to a silica gel column (400 g) prepared in acetonitrile. The column is eluted by using mixtures acetonitrile:water of increasing water content (from 0% to 15%) and the eluted fractions are discarded.

Then, the column is developed by eluting with mixtures of acetonitrile:water with a linear gradient from 85:15 to about 70:30 (v/v), at a rate of 357 ml/h.

Fractions of 25 ml are collected. The fractions which contain antibiotic L 17054 (fractions 350 to 400) are combined.

n.Butanol is then added to the pooled fractions and the mixture is concentrated to give a water satured butanol solution. After cooling to about 10° C., a precipitate begins to form. When the precipitation is complete, the solid is separated by filtration, washed with acetone and then ether and dried under vacuum yielding pure antibiotic L 17054.

Another crop of this product is obtained by concentrating the mother liquors to remove the water completely and precipitating with acetone/ethyl ether.

EXAMPLE 3

Purification of antibiotic L 17054 by silanized silica gel column chromatography Crude antibiotic L 17054 (3 g) as obtained in Example 1 is suspended in a mixture of 0.2% aqueous HCOONH$_4$:CH$_3$CN 95:5 (v/v) (150 ml).

The pH is brought to about pH 7.5 with 1N NaOH and the product is dissolved. The resulting solution is applied to a column containing 150 g of 0.06–0.2 mm silanized silica gel Merck prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel in distilled water. After washing with distilled water until the salts are completely eliminated the product is eluted with a 1:1 (v/v) CH$_3$CN:H$_2$O mixture.

The collected solution is concentrated under vacuum to a small volume, acidified to pH 3.5 with 1N HCl and the antibiotic is precipitated by adding acetone. After drying at room temperature, 0.9 g of pure antibiotic L 17054 is obtained.

We claim:

1. An essentially pure antibiotic L 17054 or a pharmaceutically acceptable salt thereof which has the following characteristics, in the non-salt form:
   (a) the specific rotation $[\alpha]_D^{20}$ is $-34°$ (c=1%, DMF)
   (b) it is freely soluble in water at pH >8.0, in dimethylformamide, dimethylsulfoxide, propyleneglycol and methylcellosolve; slightly soluble in methanol; almost insoluble in ethyl ether and acetone;
   (c) an ultraviolet absorption spectrum which has the following absorption maxima:
   in 0.1N hydrochloric acid:
   $\lambda_{max}$ 278 nm (E$_{1\ cm}^{1\%}$=60.6)
   in 0.1N sodium hydroxide:
   $\lambda_{max}$ 297 nm (E$_{1\ cm}^{1\%}$=118.8)
   in phosphate buffer pH 7.4:
   $\lambda_{max}$ 277 nm (E$_{1\ cm}^{1\%}$=70.3)
   (d) an infrared absorption spectrum in nujol with the following absorption maxima (cm$^{-1}$): 3700–2000, 2970–2850 (nujol), 1655, 1610, 1595, 1515, 1490, 1460 (nujol), 1375 (nujol), 1300, 1230, 1145, 1060, 1020, 970, 890, 850, 820
   (e) an elemental analysis, after the sample has been previously dried at about 140° C. under inert atmosphere (weight loss=7.8%), which indicates the following approximate percentage composition (average): carbon 55.46%; hydrogen, 4.50%; nitrogen 7.20%; chlorine 4.67%; ashes 0.2%
   (f) it has the following R$_f$ values in the TLC systems indicated below:

| Elution system (v/v) | R$_f$ value |
|---|---|
| (I) Acetonitrile:water 75:25 (silica gel Merck 60 F$_{254}$) | 0.32 |
| (II) Acetonitrile:5% aqueous sodium sulfate 30:70 (silica gel Merck silanized 60 F$_{254}$) | 0.61 |

Visualization: UV-light at 254 nm; 3% ethanolic ninhydrine; 1% methanolic fluorescamine;
   (g) a retention time (t$_R$) of 8.3 minutes when analyzed by HPLC using a 150×4.0 mm column Zorbax ® ODS (5–6 μm) (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$:acetonitrile (9:1) buffered at pH 6.0 with 0.1N NaOH; solution B: 25 mM NaH$_2$PO$_4$:acetonitrile (3:7) buffered at pH 6.0 with 0.1N NaOH), with a flow rate of 2 ml/min.; (internal standard: 3,5-dihydroxytoluene t$_R$ 5.60 minutes)
   (h) the $^1$H NMR spectrum registered at 270 MHz in DMSO-d$_6$ at 60° C. and with a sample concentration of 20 mg/ml is reported in FIG. 3 (Internal standard, TMS δ=0.00 ppm)
   Some of the $^1$H NMR data obtained after D$_2$O exchange and selective decoupling experiments are as follows (δ ppm, multiplicity): 1.88, s; 2.85, d; ~3.5, dd; 3–4; 4.20, d; 4.48, d; 4.50, d; 4.62, s; 4.96, ddd; 5.18, d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d (i) a potentiometric titration profile which shows three titration slopes with pH½ values equal to 5.0 (one equivalent), 7.0 (one equivalent), and 11 (five equivalents) in methylcellosolve:water 4:1 upon titration with 0.01N NaOH of the solution of the test compound containing an excess of 0.01N HCl in the same solvent mixture (l) an acidic function capable of forming salts (m) a basic function capable of forming salts (n) two sugar residues which are D-mannose and N-acetyl-D-glycosamine.

2. Antibiotic L 17054 or a pharmaceutically acceptable salt thereof, which has the following formula, in the non-salt form:

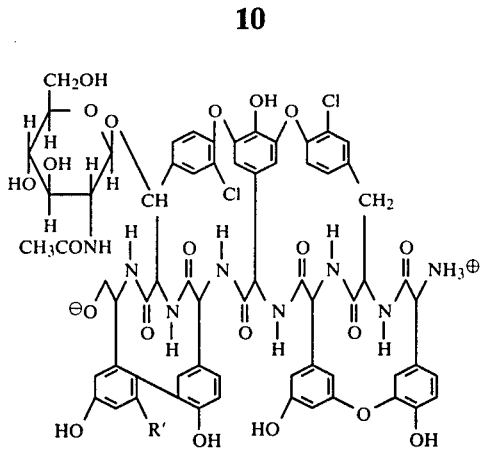

wherein R' represents the group of formula

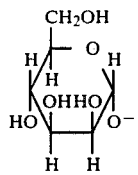

* * * * *